US009389187B2

(12) United States Patent
Furnas (10) Patent No.: US 9,389,187 B2
(45) Date of Patent: Jul. 12, 2016

(54) GLASS-SHEET OPTICAL INSPECTION SYSTEMS AND METHODS WITH ILLUMINATION AND EXPOSURE CONTROL

(71) Applicant: William John Furnas, Elmira, NY (US)

(72) Inventor: William John Furnas, Elmira, NY (US)

(73) Assignee: CORNING INCORPORATED, Corning, NY (US)

(*) Notice: Subject to any disclaimer, the term of this patent is extended or adjusted under 35 U.S.C. 154(b) by 317 days.

(21) Appl. No.: 13/689,190

(22) Filed: Nov. 29, 2012

(65) Prior Publication Data

US 2014/0146165 A1    May 29, 2014

(51) Int. Cl.
*G01N 21/896*    (2006.01)

(52) U.S. Cl.
CPC .................................... *G01N 21/896* (2013.01)

(58) Field of Classification Search
CPC ....................................................... H04N 7/18
See application file for complete search history.

(56) References Cited

U.S. PATENT DOCUMENTS

| 5,717,780 | A * | 2/1998 | Mitsumune et al. ........... 382/141 |
| 2005/0040338 | A1* | 2/2005 | Weiss et al. ................. 250/358.1 |
| 2007/0014195 | A1* | 1/2007 | Annighofer ............ G01N 27/84 369/13.02 |
| 2008/0062422 | A1* | 3/2008 | Thomas ............... G01N 21/958 356/432 |
| 2010/0034529 | A1* | 2/2010 | Jelinek ..................... G02B 7/36 396/95 |
| 2010/0074515 | A1* | 3/2010 | Zhao ....................... G01N 25/72 382/149 |
| 2010/0296084 | A1* | 11/2010 | Berg .................... G01N 21/896 356/239.1 |

* cited by examiner

*Primary Examiner* — Thai Tran
*Assistant Examiner* — Christopher T Braniff
(74) *Attorney, Agent, or Firm* — Kevin M. Able (57) ABSTRACT

Optical inspection systems and methods for inspecting a glass sheet for defects are disclosed. The systems and methods employ a digital camera and a plurality of different types of illumination sources. The object plane of the digital camera moves through the glass sheet body while flash exposures from one or more of the illumination sources are performed. The movement occurs during a ready-to-acquire time of the digital camera. This allows the digital camera to capture a plurality of digital inspection images on the fly at different exposure positions within the glass sheet body without waiting for any digital image processing to occur. The digital inspection images are then reviewed to characterize any revealed defects.

18 Claims, 7 Drawing Sheets

GLASS-SHEET OPTICAL INSPECTION SYSTEMS AND METHODS WITH ILLUMINATION AND EXPOSURE CONTROL

FIELD

The present disclosure relates to the optical inspection of glass, and in particular relates to optical inspection systems and methods for performing optical inspection of glass sheets with illumination and exposure control.

BACKGROUND

Optical display glass is formed in large sheets on a glass manufacturing line. The display glass needs to be inspected for defects or manufacturing anomalies prior to being further processed and included in any one of a variety of display devices. The inspection is typically optically based and usually performed in two steps: a coarse optical inspection that covers the entire glass sheet to identify locations that need to be revisited for closer inspection; and a revisit optical inspection that takes a closer look at the locations identified in the course inspection.

The revisit inspection is performed using an optical inspection system called a micro revisit station or MRS. The MRS acquires multiple images of the problematic location on the glass sheet. The multiple images are taken under different illumination conditions and at different locations at the surfaces and within the glass sheet so that the potential defect or anomaly can be more easily detected, located and characterized.

A main consideration in the optical inspection process performed by the MRS is speed. Delays in the optical inspection process result in manufacturing process delays. Such delays also prevent timely manufacturing information from being fed back into the upstream manufacturing process to allow for adjusting the manufacturing process to avoid the formation of the identified defects.

SUMMARY

An aspect of the disclosure is a method of inspecting a glass sheet having a body with a thickness and front and back surfaces to find at least one glass defect. The method includes aligning a digital camera with an inspection region of the glass sheet that contains the at least one defect, the camera having an object plane, a depth of field DOF and a ready-to-acquire time $T_{RA}$. The method also include moving the digital camera to capture a plurality of digital inspection images of the inspection region for different exposure positions within the glass sheet body by performing a plurality of flash exposures of illumination light from at least one type of illumination source, including performing the moving during the ready-to-acquire time $T_{RA}$. The method further includes reviewing the plurality of digital inspection images to characterize the defect.

Another aspect of the disclosure is a method of inspecting a glass sheet having a body with a thickness and front and back surfaces to find at least one glass defect. The method includes aligning a digital camera with an inspection region of the glass sheet that contains the at least one defect, the camera having an object plane and a depth of field DOF. The method also includes continuously moving the digital camera at a velocity v so that the object plane moves through the body of the glass sheet from the front surface to the back surface. The method further includes capturing a plurality of digital inspection images of the inspection region for different positions within the glass sheet body during said continuous moving of the digital camera by performing a plurality of flash exposures of duration δt of illumination light from at least one type of illumination source, wherein $v \cdot \delta t < k \cdot DOF$, for $0.1 < k < 0.75$. The method also includes reviewing the plurality of digital inspection images to characterize the defect.

Another aspect of the disclosure is an optical inspection system for capturing inspection images of a glass sheet having a body with a thickness and front and back surfaces. The system includes a digital camera operably disposed adjacent the front surface of the glass sheet at an inspection region, the camera having a depth of field DOF, an object plane and a ready-to-acquire time. The system also includes a stage that supports the digital camera. The stage is movable to move the object plane from the front surface to the back surface of the glass sheet through a plurality n of exposure positions within the glass sheet body. The system also has a plurality of illumination sources operably arranged to illuminate the inspection region of the glass sheet, with each illumination source configured to provide a different type of illumination from the other illumination sources. The system additionally includes a microcontroller operably connected to the digital camera, to the plurality of illumination light sources and to the movable stage. The microcontroller is configured to initiate the movement of the stage and also to cause a plurality n of flash exposures from at least one of the illumination sources for each flash exposure so that the digital camera captures n digital inspection images at the n exposure positions within the glass sheet body, wherein the movement of the movable stage occurs during the ready-to-acquire time of the digital camera.

Additional features and advantages will be set forth in the Detailed Description that follows and in part will be readily apparent to those skilled in the art from the description or recognized by practicing the embodiments as described in the written description and claims thereof, as well as the appended drawings. It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute a part of this Detailed Description.

The entire disclosure of any publication or patent document mentioned herein is incorporated by reference.

Cartesian coordinates are shown in some of the Figures for the sake of reference and are not intended to be limiting as to direction or orientation.

Figure 1:
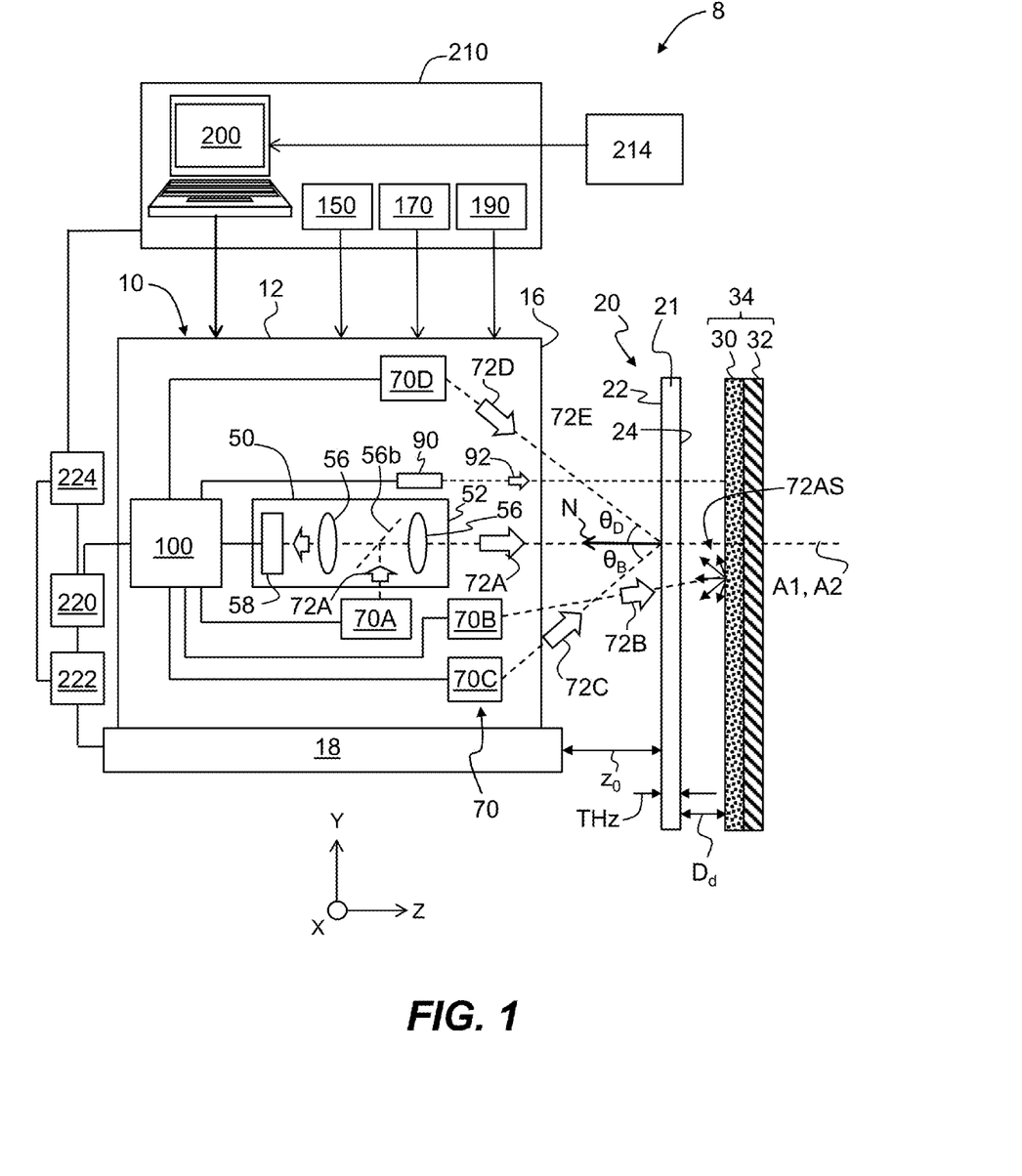
FIG. 1 and FIG. 2 are schematic diagrams of an example optical inspection station that includes an optical inspection system operably disposed relative to a glass sheet to be inspected for defects.
Figure 2:
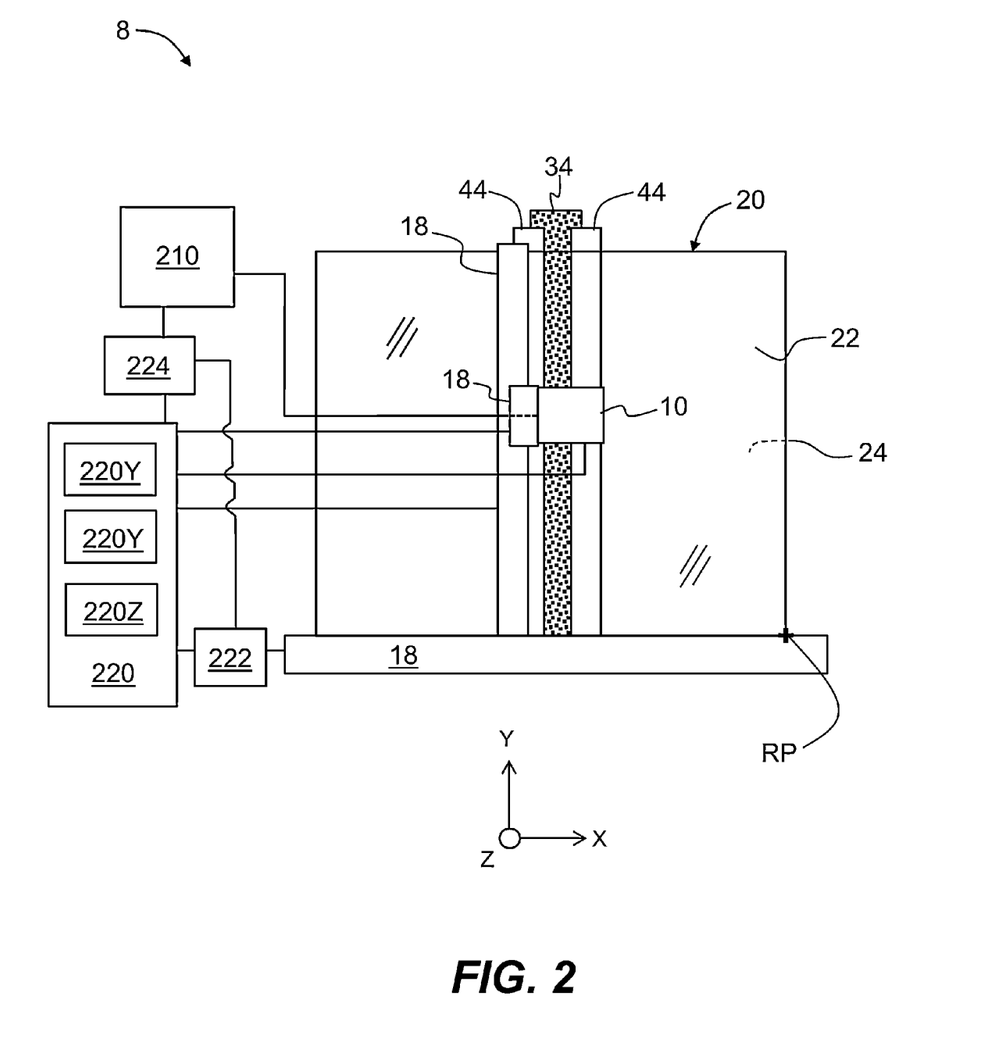
Figure 3:
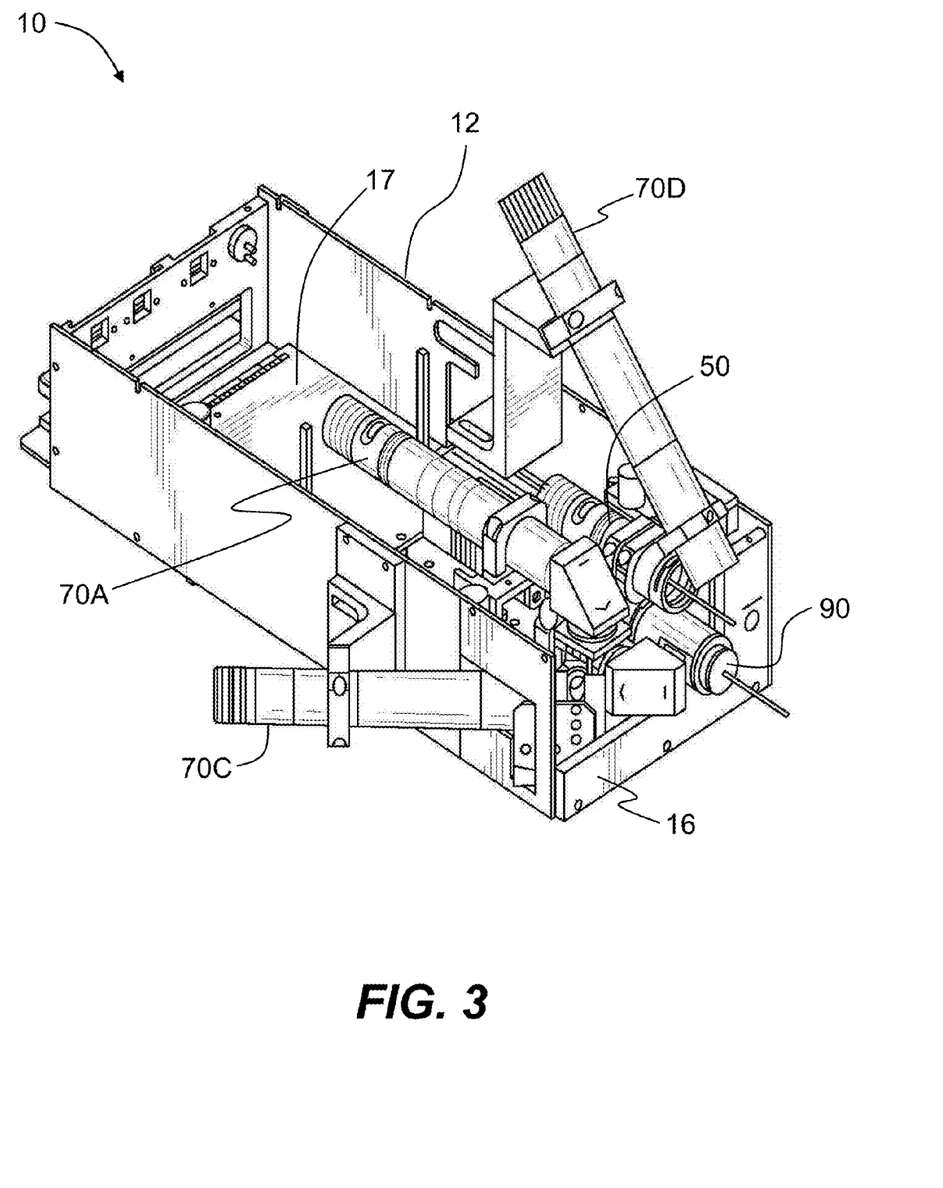
FIG. 3 is an elevated view of an example configuration of the optical inspection system.

FIG. 1 and FIG. 2 are schematic diagrams of an example optical inspection station 8 that includes an optical inspection system ("system") 10 operably disposed relative to a glass sheet 20 to be inspected for defects. The optical inspection system 10 is an example of the aforementioned MRS. FIG. 3 is an elevated view of an example configuration of system 10. The system 10 includes a housing 12 that is supported on a movable stage 18 that can move in three dimensions as indicated by the reference Cartesian coordinates. The housing 12 has a front end 16. FIG. 3 shows a circuit board 17 within housing 12 that in an example includes at least some of the various electronic components discussed below.

Figure 4:
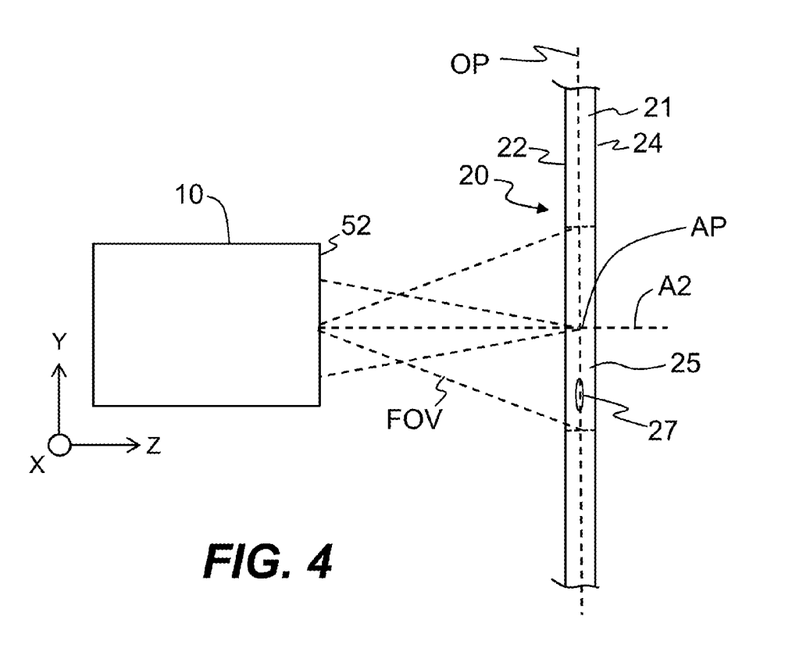
FIG. 4 is a schematic side view of the optical inspection system and glass sheet being inspected, illustrating the field of view FOV of the optical inspection system and a defect located in the region of the glass sheet being inspected.
Figure 5:
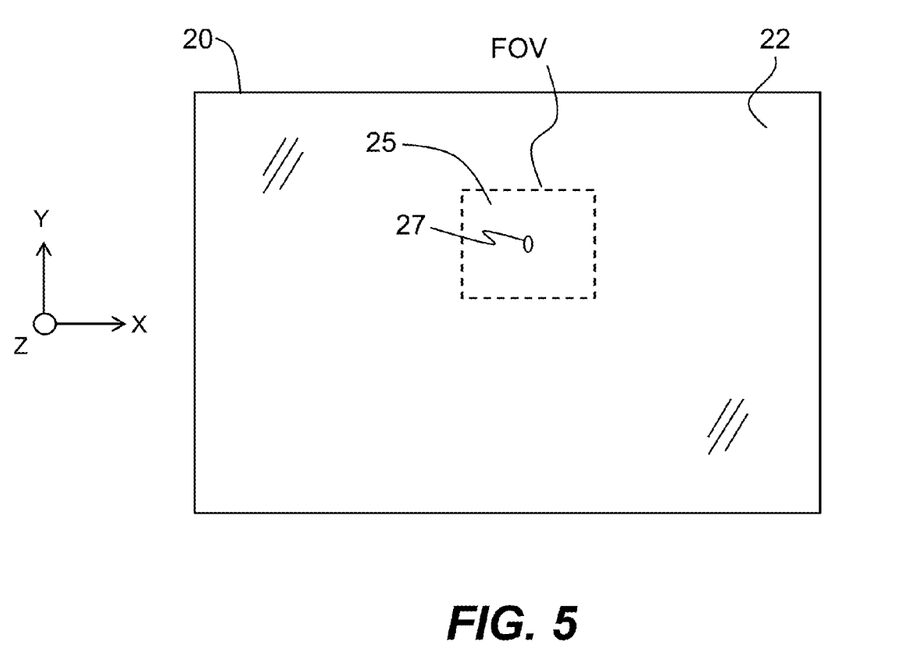
FIG. 5 is a front-on view of the glass sheet showing the field of view FOV and the region of the glass sheet being inspected.

FIG. 4 is a schematic side view of system 10 and glass sheet 20 that is being inspected, illustrating the field of view FOV of the optical inspection system and a defect 27 located in an inspection region 25 of the glass sheet. FIG. 5 is a front-on view of glass sheet 20 showing the field of view FOV and inspection region 25 of the glass sheet.

The glass sheet 20 has a body 21 that defines a front surface 22 and a back surface 24. The inspection region 25 is a volume within glass sheet body 21 and in an example is defined by the field of view FOV in the X-Y plane and a glass thickness THz in the Z-direction. This is because defect 27 can reside anywhere between front surface 22 and back surface 24 of glass sheet 20 and can also be located on the front or back surface or can extend from the front or back surface well into body 21.

With reference to FIGS. 1 through 5, glass sheet 20 is operably supported adjacent front end 16 of system 10 and along a system axis A1 in an X-Y plane by a support device 44. The thickness THz of glass sheet body 21 is substantially constant and in an example ranges from a few millimeters to less than 0.1 mm. In an example, system axis A1 makes a right angle with front surface 22 of glass sheet 20. In an example, support device 44 holds glass sheet 20 at back surface 24 by constraining the glass sheet with vacuum and floating with the glass sheet on an air cushion (not shown).

A diffuser 30 and a mirror 32 are also arranged along axis A1 and in the X-Y plane, with the diffuser residing adjacent the mirror and between the mirror and back surface 24 of glass sheet 20. The diffuser 30 is placed against mirror 32. The combination of diffuser 30 and mirror 32 define a reflective diffuser 34. The reflective diffuser 34 is spaced apart from back surface 24 of body 21 by a distance $D_d$ of about 90 mm.

With reference in particular to FIG. 1, system 10 includes a digital camera ("camera") 50 that has a front end 52 and a camera axis A2 that lies along (i.e., is coaxial with) system axis A1. The camera 50 includes imaging lenses 56, two of which are shown by way of illustration. The lenses 56 may each consist of one or more lens elements or optical elements. The camera 50 also includes an image sensor 58, such as a CMOS sensor or CCD array that digitizes the image formed by lenses 56 to form a digital image. An example resolution of image sensor 58 is in the range from 5 mega pixels to 8 mega pixels.

As explained in greater detail below, camera 50 captures digital images that serve as inspection images, i.e., they can be reviewed (e.g., displayed for a user to see or for a computer to process) to characterize any defects 27 that show in one or more of the inspection images. These digital images are referred to hereinafter as "digital inspection images."

With reference to FIGS. 4 and 5, camera 50 has a field of view FOV that in part defines inspection region 25 on glass sheet 20. In an example, field of view FOV is about 3,296 mm×2,472 mm, so that 1 pixel of image sensor 58 represents about 1 μm of glass sheet 20 in inspection region 25. An example image capture rate for camera 50 is in the range from about 8 frames per second (fps) to 17 fps (125 milliseconds (ms) to 58 ms), with an exposure time δt ranging from 8 ms to 22 ms. In a typical vision system, the time from exposure to the image being available in memory is on the order of hundreds of milliseconds, which is much slower than the frame rate. However, camera 50 of system is ready for the next exposure at a ready-to-acquire time $T_{RA}$ that is essentially the same as the frame rate, and motion subsystems can engage immediately at the conclusion of an exposure to prepare for the next exposure.

An example camera 50 has a data transfer rate via an Ethernet Cat 6 cable of 240 MB/s. The camera 50 is configured to image over a range of wavelengths, e.g., over wavelengths or bands in the visible spectral range. In an example, camera 50 has a depth of field DOF of about 25 microns to about 100 microns. The depth of field DOF is measured from an object plane OP that has an on-axis position AP. The defect 27 is shown within inspection region 25 in body 21 of glass sheet 20. In FIG. 4, object plane OP is shown as being coincident with defect 27.

The system 10 also includes a plurality of illumination sources 70 (see also FIG. 6), with four such illumination sources being shown and identified as 70A through 70D. The first illumination source 70A emits light 72A of a first wavelength $\lambda_1$, such as green light, e.g., light in the wavelength range between 520 nm and 530 nm. A beam-splitting element 56b is arranged along camera axis A2 between the two lens elements 56 and is used to direct light 72A along the camera axis to glass sheet 20.

The second illumination source 70B emits light 72B of a second wavelength $\lambda_2$, such as red light, e.g., light in the wavelength range between 615 nm and 631 nm. Moreover, in an example, second illumination source 70B is configured such that light 72B is scattered by diffuser 34 and forms scattered light 72AS that defines a graded illumination of glass sheet 20 with the camera field of view.

The third illumination source 70C emits light 72C of a third wavelength band $\Delta\lambda_3$, such as white light, e.g., light in the visible wavelength range between about 400 nm and about 750 nm. The third illumination source 70C is configured to provide a first dark-field illumination of glass sheet 20 at a first incident angle relative to camera 50.

The fourth illumination source 70D emits light 72D of a fourth wavelength band $\Delta\lambda_4$, such as white light, e.g., light in the visible wavelength range between about 400 nm and about 750 nm. In an example, $\Delta\lambda_3=\Delta\lambda_4$. The fourth illumination source 70D is configured to provide a second dark-field illumination of glass sheet 20 at a second incident angle relative to camera 50.

Figure 6:
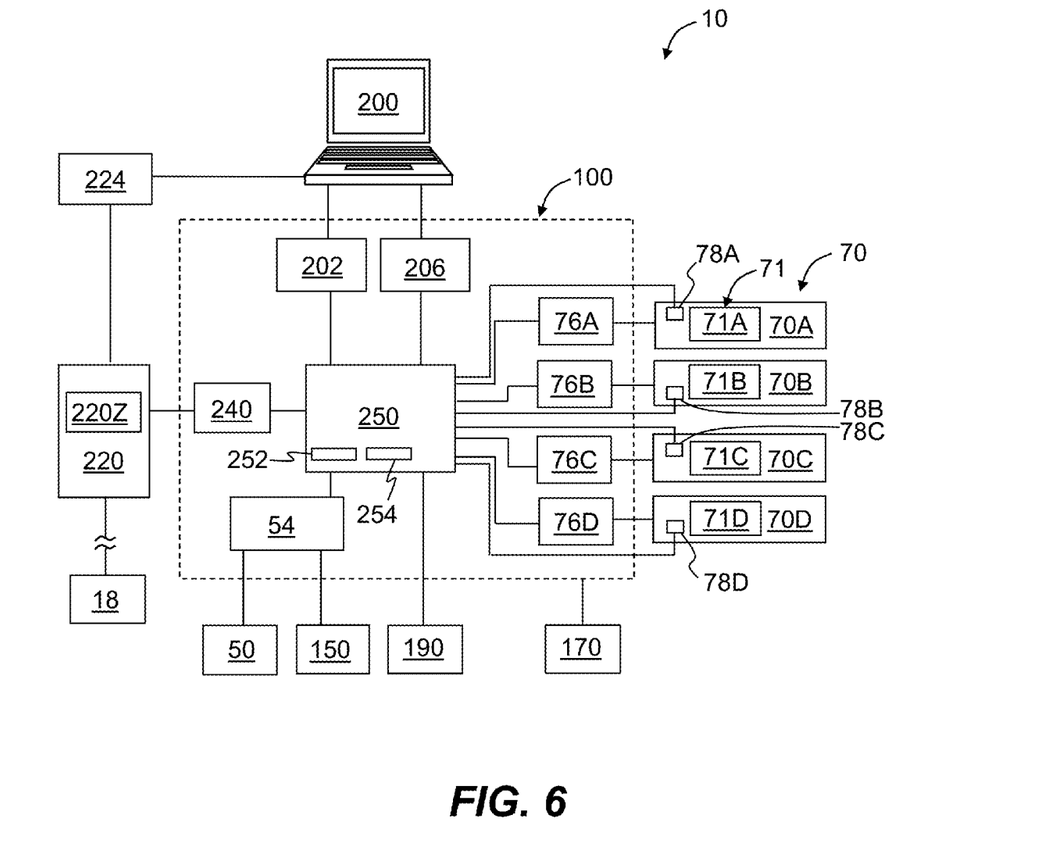
FIG. 6 is a schematic diagram of the main controller of the optical inspection system along with the main components to which the main controller is attached.

Thus, in an example, each illumination source 70 is a different type of illumination source in that each provides a different type of illumination than the other. In another example, such as is shown in FIGS. 1 and 6, two of the illumination sources 70 provide the same type of illumination but have different configurations. For example, the two dark-field illumination sources 70C and 70D can have different incident angles $\theta_B$ and $\theta_D$ relative to a surface normal N of glass sheet 20 (FIG. 1).

In an example embodiment shown in FIG. 6 (introduced and discussed below), one or more of illumination sources 70 include a light-emitting diode (LED) 71 that emits the corresponding wavelength or wavelength band of light 72.

With reference again to FIG. 1, system 10 also includes an alignment light source 90 that emits alignment light 92. In an example, alignment light source 90 includes a laser. The alignment light source 90 is configured such that alignment light 92 provides an alignment reference for camera 50 so that the position of glass sheet 20 and of mirror 32 relative to a reference position RP can be ascertained. In an example, reference position RP has (x, y, z) coordinates $(x_R, y_R, z_R)$, where $x_R, y_R, z_R$ are three spatial reference coordinates. In an example, $(x_R, y_R, z_R)=(0,0,0)$.

The illumination sources 70 and alignment light source 90 are electrically connected to a controller 100 configured to control the operation of these components in order to carry out the inspection methods, as described below.

With reference to FIGS. 1 and 2, optical inspection station 8 includes an external controller 200, a camera power supply 150, an illuminator source power supply 170 and an alignment light source and microcontroller power supply 190, all of which are operably connected to system 10. In an example, some or all of these components are arranged in a storage unit (e.g., rack, cabinet, etc.) 210. The external controller 200 may be connected to an external device 214, such as a computer, server or database, that provides initial inspection information to the external controller. In an example embodiment, this information is used to control the optical inspection of glass sheet 20 as carried out by system 10 and in particular identifies inspection region 25.

The optical inspection station 8 also includes a motor encoder 220 and a precision drive motor 222. The motor encoder 220 is electrically connected to controller 100 and to precision drive motor 222. The precision drive motor 222 is operably connected to movable stage 18 and is configured to cause the movable stage to move in very precise increments. A motion control subsystem 224 is operably connected to external controller 200 as well as to motor encoder 220 and precision drive motor 222 and serves to manage the operation of the latter two components. FIG. 1 shows stage 18 located a reference distance $z_0$ away from front surface 22 of glass sheet 20.

The motor encoder 220 is configured to assist in controlling the operation of precision drive motor 222 and to provide controller 100 with a precise measurement of the motor position (e.g., shaft or rotor position). The motor encoder 220 includes a Z-axis motor encoder 220Z (see FIG. 6) that allows the Z-position of moveable stage 18 (and thus system 10) to be precisely known and controlled relative to reference position RP.

In an example, precision drive motor 222 is configured to provide either continuous movement or stepped movement of moveable stage 18. In one example, precision drive motor 222 does not stop during an exposure by one or more illumination sources 70 and then start again to move to a position for the next exposure. The precision drive motor 222 may move stage 18 in discrete increments, but these increments are very small compared to the distance between exposures, as explained below. Thus, for practical purposes, the movement of stage 18 is considered to be continuous when precision drive motor 222 is turned on even though strictly speaking it may be moving in very small increments ("micro-increments"). The very small increments are recorded by the Z-axis motor encoder 220Z.

In the other embodiment wherein stage 18 starts and stops, the stage typically moves over many micro-increments before stopping at discrete locations. The two main methods of operation, namely continuous operation and incremental (or stepped) operation, are discussed in greater detail below.

FIG. 6 is a schematic diagram of system 10 that shows more details of controller 100. The controller 100 includes a microcontroller 250 that is operably connected to LED driver units 76A through 76D, which in turn are electrically connected to illuminator sources 70A through 70E. In an example, LED driver units 76A through 76D, each LED driver unit including an isolated current monitor and an optical isolator (not shown). In an example, an exemplary LED driver for LED driver units 76 is LED driver part #LM3433 from National Instruments, Inc.

The microcontroller 250 includes a processor 252, memory 254 and input/output peripherals (not shown). The microcontroller 250 is programmable to carry out the methods described herein. In an example, microcontroller 250 is programmable through external controller 200 and receives and stores instructions and information from the external controller in memory 254 as well as in processor 252. The processor 252 and memory 254 constitute computer-readable media for storing the aforementioned instructions for carrying out the optical inspection methods disclosed herein. The external controller 200 also includes computer-readable media (not shown) for storing instructions used in the operation of system 10.

The illumination sources 70 each include a corresponding LED 71, e.g., LEDs 71A through 71D. The LED drivers 76A through 76D are electrically connected to illuminator source power supply 170, with the LED drivers ultimately providing the high-current power to their respective LEDs 71A through 71D. The illumination sources 70A through 70D include respective temperature sensors 78A through 78D electrically connected to microcontroller 250 and configured to monitor the respective temperatures of LEDs 71A through 71D. In an example, temperature sensors 78A through 78D are thermistors. The microcontroller 250 can set the actual combination and duration of illumination for a particular exposure in the first few microseconds of the exposure signal from camera 50. Thus, there is no need for a delay (i.e., a settling time) for a change in illumination power supply, which can represent a savings of potentially several hundred milliseconds per change.

The controller 100 also includes a camera input/output (I/O) unit 54 that is operably connected to microcontroller 250, camera 50 and camera power supply 150. The camera I/O unit 54 manages the communication of data between camera 50 and microcontroller 250, and also manages the flow of power from camera power supply 150 to the camera. The alignment light source and microcontroller power supply 190 is operably connected to microcontroller 250 and provides electrical power thereto as well as to alignment light source 90.

The controller 100 also includes an I/O unit 202 that is connected to external controller 200 and to microcontroller 250. The I/O unit 202 interfaces serial and parallel information between external controller 200 and microcontroller 250. The controller 100 also includes a USB interface 206 for programming microcontroller 250 using external controller 200.

The controller 100 also includes an isolated encoder interface unit 240 that resides between microcontroller 250 and external Z-axis motor encoder 220Z. The isolated encoder interface unit 240 serves to prevent signal irregularities from reaching microcontroller 250.

Methods of Operation

In the operation of system 10, external controller 200 initializes microcontroller 250 with information about both the sequences of images to be taken by camera 50 while still and the sequences of images to be taken while moving. This information includes intensity, duration and combinations of sources. For a specific inspection, external controller 200 receives information from external device 214 regarding the general (coarse) inspection of glass sheet 20. The external controller 200 directs motion control subsystem 224 to position system 10 via moveable stage 18 to image inspection region 25 of glass sheet 20 as identified by the coarse inspection.

The motion control subsystem 224 then indicates to external controller 200 that inspection region 25 is identified and is within the field of view FOV, with front surface 22 of glass sheet 20 within depth of field DOF of camera 50. Then, external controller 200 sends a signal to controller 100 to activate at least one illumination source 70, and camera 50 captures a first image of front surface 22 of glass sheet 20 over inspection region 25. In an example, camera 50 informs controller 100 when it is ready to acquire a new image, and controller 100 passes this information along to external controller 200.

In an example, external controller 200 configures the illumination setting and instructs controller 100 to capture a second image of front surface 22 of glass sheet 20 over inspection region 25 using a different illumination from an illumination source or sources 70 than that used for the first image. Alternatively, external controller 200 configures controller 100 with an illumination configuration for the two images to be taken of front surface 22. Then, once motion control subsystem 224 indicates that the motion is complete, external controller 200 instructs controller 100 to acquire the pair of images via activation of camera 50 and the particular illumination sources 70.

Next, camera 50 indicates when the exposures are complete. The microcontroller 250 then sends a control signal to external controller 200, which directs motion control subsystem 224 to initialize Z-axis motion. The motion position change is transmitted from Z-axis motor encoder 220Z via isolated encoder interface unit 240 to microcontroller 250. This position change occurs while the image data is being transferred from camera 50 to external controller 200 so that there is minimum delay in carrying out the measurement.

As discussed above, in one example embodiment, stage 18 is moved in the Z-direction at a constant velocity v, such as 1 mm/s to 2 mm/s. The Z-axis motor encoder 220Z precisely tracks the movement of stage 18 by the micro-increments of the movement and sends this information to microcontroller 250. The microcontroller 250 also causes camera 50 and one or more illumination sources 70 to be activated to perform exposures E of glass sheet 20 as a function of distance z into glass sheet body 21.

The exposures E occur while stage 18 continually moves in the Z-direction. The one or more illumination sources 70 are activated by microcontroller 250 to provide a series of "flash" exposures E that, in an example, have a duration δt of between about 1.5 ms to about 6 ms. For a 3-ms duration δt of flash exposure E and a stage velocity v in the z-direction of 1 mm/s, the object plane moves by $dz = v \cdot \delta t = (1 \text{ mm/s})(3 \text{ ms}) = 3$ microns during the exposure. This distance is well within depth of field DOF of camera 50. In an example, depth of field DOF is in the range from 20 microns to 50 microns and in another example is in the range from 25 microns to 40 microns. In an example embodiment, $v \cdot \delta t < \text{DOF}$, and in another example embodiment, $v \cdot \delta t < k \cdot \text{DOF}$, where $0.1 < k < 0.75$.

In another embodiment discussed above, stage 18 stops to take an exposure. This method is based on the fact that camera 50 needs the aforementioned ready-to-acquire time $T_{RA}$ between exposures so that the data captured by image sensor 58 can be transmitted and the image sensor can sense the next image. The ready-to-acquire time $T_{RA}$ is thus the amount of time $DT_E$ between exposures one has to wait before camera 50 is ready to acquire another image, i.e., perform another exposure. In certain cases, stage 18 can arrive at the designated exposure position before the ready-to-acquire time $T_{RA}$ has passed. In this case, stage 18 stops at the designated exposure position and after the ready-to-acquire time $T_{RA}$ has passed (i.e., immediately thereafter or as soon as possible thereafter), camera 50 performs the exposure and the stage starts moving again to bring the camera to the next designated exposure position.

Note that there is no delay in moving stage 18 due to the transfer of image data from image sensor 58. The only delay in taking exposures to capture digital images is the ready-to-acquire time $T_{RA}$ of camera 50. In other words, system 10 can operate as fast as possible, since the ready-to-acquire time $T_{RA}$ is the only fundamental gating factor that determines the fastest measurement speed of the system.

Figure 7:
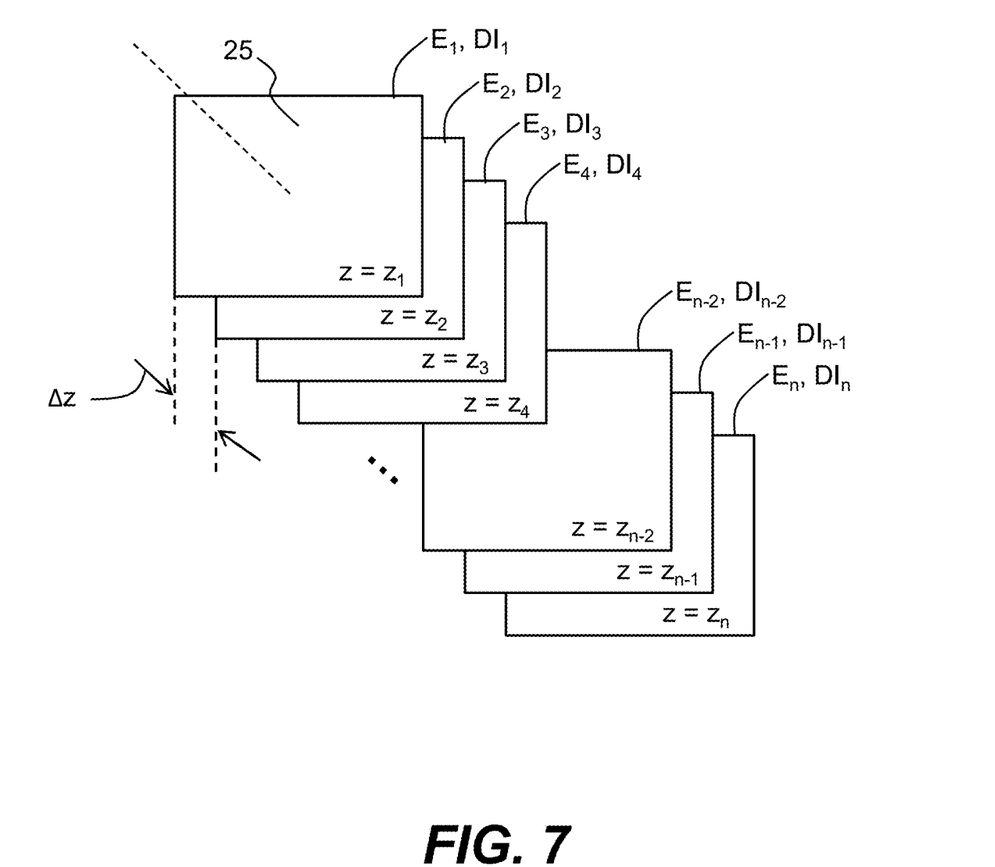
FIG. 7 and FIG. 8 are example sequences of schematic digital inspection images obtained using the optical inspection system, with FIG. 8 showing how an example defect can reveal itself as a function of distance into the glass body as the images are obtained.

The microcontroller 250 can be programmed to carry out essentially any sequence of exposures using one or more illumination sources 70 for each exposure as a function of distance z into glass sheet body 21. The result is a series of n captured digital inspection images DI (i.e., $DI_1, DI_2, \ldots DI_n$) for select exposures E ($E_1, E, \ldots E_n$) from one or more illumination sources 70 through glass sheet body 21 as a function of distance z for n locations ($z_1, z_2, \ldots z_n$), as schematically illustrated in FIG. 7. An example number n is in the range from 1 to 32. The time between exposures is $\Delta t_E$, and the time of each exposure is δt. It is noted that δt need not be the same for each exposure, and the situation where δt is the same for all of the exposures is a special case. The time at which a given exposure starts is $t_E$. The physical distance between exposure positions is Δz.

For an example glass sheet 20 having a thickness TH$z$=700 microns, an exemplary number n is 10. Since the time $t_E$ at which exposures E occur can be varied, the distance Δz between adjacent exposures can be varied. Thus, digital inspection images DI need not be associated with evenly spaced z positions within glass sheet body 21. In addition, system 10 can be operated to perform a combination of continuous stage movement and stepped stage movement for a given sequence of exposures E. In an example, the number of digital inspection images DI that are captured is in the range from 2 to 32.

Thus, in one example inspection method using system 10, the system captures two digital inspection images DI of front surface 22 of glass sheet 20, as discussed above. The first digital image DI is captured using an exposure with coaxial illumination from illumination source 70A. The second digital image DI is captured using an exposure based on a combination of gradient illumination from illumination source 70B and reflective diffuser 34, and both dark-field illumination sources 70C and 70D.

The stage 18 is then moved so that the camera focus is shifted into glass sheet body 21 and additional digital images DI are acquired. In an example, digital images DI are acquired at 6 different depths (distances) into glass sheet body 21 using a combination of gradient illumination from illumination source 70B and reflective diffuser 34, and both dark-field illumination sources 70C and 70D. Finally, on back surface 24 of glass sheet 20, a digital image DI is captured using an exposure based on a combination of gradient illumination from illumination source 70B and reflective diffuser 34, and both dark-field illumination sources 70C and 70D. An additional digital image DI of back surface 24 is captured using an exposure with coaxial illumination from illumination source 70A.

Figure 8:
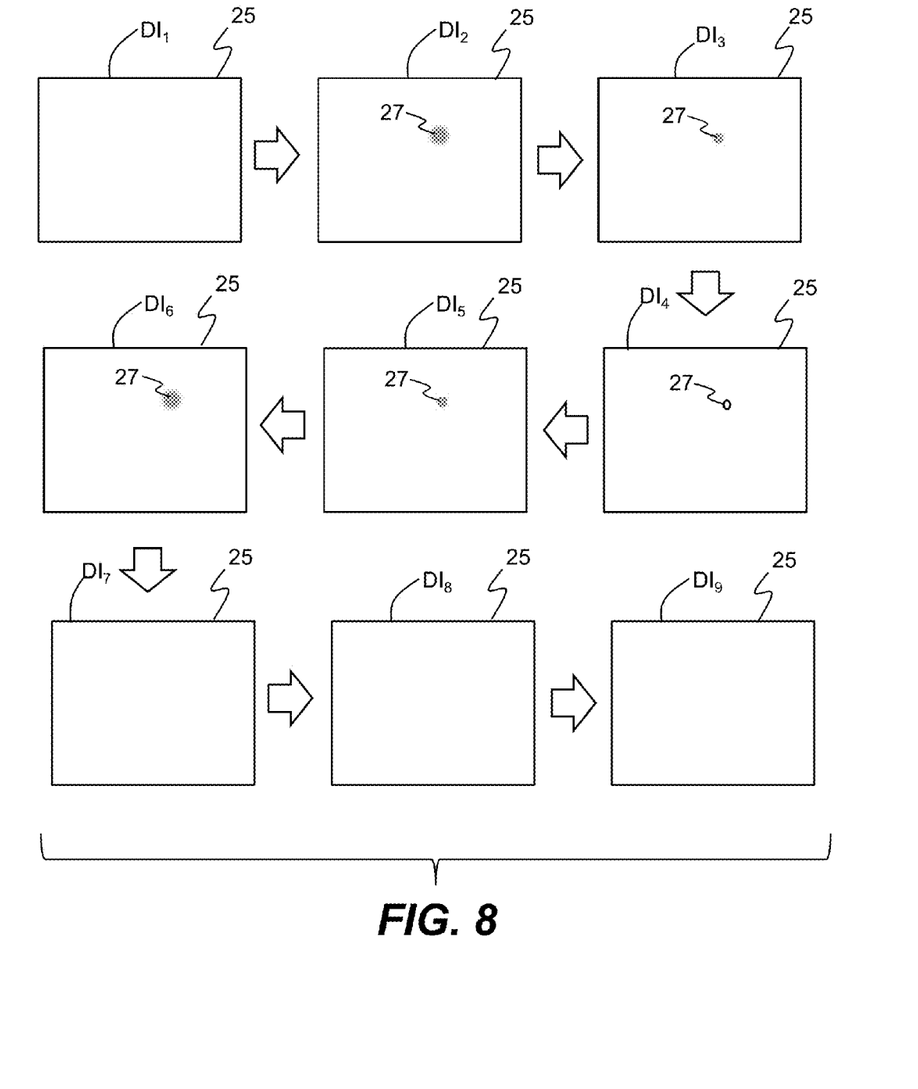

FIG. 8 illustrates a schematic example sequence of nine digital inspection images $DI_1$ through $DI_9$ of inspection region 25 showing how defect 27 can show up in a number of the digital inspection images as the sequence of images passes through the z-locations that intersect the defect. An aspect of the optical inspection methods described herein includes reviewing the plurality of digital inspection images DI to characterize defect 27. The characterization includes at least one of location, size, depth, shape and type. Types of defects 27 with an opaque or transparent character include but are not limited to scratches, bubbles, inclusions, onclusions and surface discontinuity. In the example shown in FIG. 8, defect 27 is in the form of a bubble, and digital image DI goes in and out of focus from digital image $DI_2$ through $DI_6$, with $DI_4$ representing the best-focus position.

The above-described method of operation of system 10 does not require digital inspection images DI to be stored prior to moving stage 18. Rather, digital inspection images DI are captured on the fly as stage 18 either is in motion or completes its motion in a time less than the ready-to-acquire time $T_{RA}$. This "on the fly" digital-image-capture method that utilizes fast-changing illumination takes about one third the time taken by the convention stop and shoot approach, which waits for the digital images to be stored in memory 254. The potential reduction in inspection cycle time is about 7 seconds per glass sheet 20, assuming that one average 3 revisit inspections per glass sheet are required. This represents a substantial savings of time over the course of inspecting a large number of glass sheets 20.

During the measurement process (i.e., the capturing of digital inspection images DI through glass sheet body 21), temperature sensors 78 measure the temperature of the corresponding LEDs 71 and send representative temperature signals to microcontroller 250. This allows external controller 200 to alert the operator to potential maintenance requirements or faults before a failure.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of inspecting a glass sheet having a body with a thickness and front and back surfaces to find at least one glass defect, comprising:
aligning a digital camera with an inspection region of the glass sheet that contains the at least one defect, the camera having an object plane, a depth of field DOF and a ready-to-acquire time $T_{RA}$;
moving the digital camera in a z direction along a z-axis, wherein the z direction is one of toward or away from the front surface of the glass sheet and the z-axis is substantially normal to the front surface of the glass sheet;
capturing a plurality of digital inspection images of the inspection region for different exposure positions within the glass sheet body as the digital camera is moved in the z direction along the z-axis by performing a plurality of flash exposures of illumination light from at least one type of illumination source, including performing the moving during the ready-to-acquire time $T_{RA}$; and
reviewing the plurality of digital inspection images to characterize the defect.

2. The method of claim 1, wherein moving the digital camera is performed so that the object plane moves continuously through at least one exposure position at a velocity v, and further including performing the flash exposure at the at least one exposure position through which the focal plane continuously moves with an exposure duration of $\delta t$, wherein $v \cdot \delta t < k \cdot DOF$ and k is in a range of from about 0.1 to about 0.75.

3. The method of claim 2, including moving the object plane continuously from the front surface to the back surface of the glass sheet so that the at least one exposure position through which the focal plane continuously moves consists of a plurality of exposure positions between the front and back surfaces of the glass sheet.

4. The method of claim 1, wherein the at least one type of illumination source is selected from the group of types of illumination sources comprising: an on-axis source, a first dark-field source at a first incident angle, a second dark-field source at a second incident angle and a gradient source.

5. The method of claim 1, further including at least one of:
a) capturing at least one digital inspection image of the front surface of the glass sheet; and
b) capturing at least one digital inspection image of the back surface of the glass sheet.

6. The method of claim 1, wherein the plurality of digital inspection images is in the range from 2 to 32 digital inspection images.

7. The method of claim 1, further comprising controlling a timing and a duration of the flash exposures using a microcontroller operably connected to the at least one type of illumination source and to the digital camera.

8. The method of claim 7, wherein the camera is supported by a moveable stage and further comprising:
moving the movable stage with a drive motor that is controlled by the microcontroller through a motor encoder; and
measuring the positions of the object plane within the glass body for the flash exposures relative to a reference position using the motor encoder.

9. The method of claim 1, wherein the at least one type of illumination source includes a light-emitting diode (LED), and including monitoring the temperature of the LED and controlling an amount of power provided to the LED based on the monitored temperature.

10. A method of inspecting a glass sheet having a body with a thickness and front and back surfaces to find at least one glass defect, comprising:
aligning a digital camera with an inspection region of the glass sheet that contains the at least one defect, the camera having an object plane and a depth of field DOF;

continuously moving the digital camera at a velocity v in a z direction along a z-axis, wherein the z direction is one of toward or away from the front surface of the glass sheet and the z-axis is substantially normal to the front surface of the glass sheet so that the object plane moves through the body of the glass sheet from the front surface to the back surface;

capturing a plurality of digital inspection images of the inspection region for different positions within the glass sheet body during said continuous moving of the digital camera by performing a plurality of flash exposures of duration δt of illumination light from at least one type of illumination source, wherein v·δt<k·DOF, and k is in a range of from about 0.1 to about 0.75; and reviewing the plurality of digital inspection images to characterize the defect.

11. The method of claim 10, wherein the at least one type of illumination source is selected from the group of types of illumination sources comprising: an on-axis source, a first dark-field source at a first incident angle, a second dark-field source at a second incident angle and a gradient source.

12. The method of claim 10, wherein the plurality of digital inspection images is in the range from 2 to 32 digital inspection images.

13. The method of claim 10, further comprising:
controlling a timing and a duration of the flash exposures using a microcontroller operably connected to the at least one type of illumination source and to the digital camera.

14. The method of claim 10, further including at least one of:
a) capturing at least one digital inspection image of the front surface of the glass sheet; and
b) capturing at least one digital inspection image of the back surface of the glass sheet.

15. An optical inspection system for capturing inspection images of a glass sheet having a body with a thickness and front and back surfaces, comprising:
a digital camera operably disposed adjacent the front surface of the glass sheet at an inspection region, the camera having a depth of field DOF, an object plane and a ready-to-acquire time $T_{RA}$;
a stage that supports the digital camera, the stage being movable to move the object plane from the front surface to the back surface of the glass sheet through a plurality n of exposure positions within the glass sheet body;
a plurality of illumination sources operably arranged to illuminate the inspection region of the glass sheet, with each illumination source configured to provide a different type of illumination from the other illumination sources; and
a microcontroller operably connected to the digital camera, to the plurality of illumination light sources and to the movable stage, the microcontroller being configured to initiate continuous movement of the stage in a z direction along a z-axis, wherein the z direction is one of toward or away from the front surface of the glass sheet and the z-axis is substantially normal to the front surface of the glass sheet, and also to cause a plurality n of flash exposures from at least one of the illumination sources for each flash exposure so that the digital camera captures n digital inspection images at the n exposure positions within the glass sheet body during continuous movement of the stage in the z direction along the z-axis.

16. The optical inspection system of claim 15, wherein the microcontroller is configured to cause the movable stage to move continuously through one or more of the exposure positions at a velocity v, wherein the flash exposures have a duration δt at the one or more exposure positions, and wherein v·δt<k·DOF, and k is in a range of from about 0.1 to about 0.75.

17. The optical inspection system of claim 15, further including:
a drive motor operably connected to the movable stage and operably connected to the microcontroller via a motor encoder, the movable stage being configured to cause the continuous movement of the object plane of the camera, and the motor encoder being configured to provide motor information to the microcontroller, wherein the microcontroller is configured to determine the positions of the n object planes within the glass body relative to a reference position.

18. The optical inspection system of claim 15, further including an external controller operably connected to the microcontroller and configured to control the operation of the microcontroller.

* * * * *